United States Patent
Albertelli

(10) Patent No.: US 8,240,307 B2
(45) Date of Patent: Aug. 14, 2012

(54) APPARATUS FOR NON-INVASIVE MECHANICAL VENTILATION

(75) Inventor: Roberto Albertelli, Tirrenia (IT)

(73) Assignee: Azienda Ospedaliera Pisana, Pisa (IT)

( * ) Notice: Subject to any disclaimer, the term of this patent is extended or adjusted under 35 U.S.C. 154(b) by 720 days.

(21) Appl. No.: 10/557,064

(22) PCT Filed: May 14, 2004

(86) PCT No.: PCT/EP2004/005231
§ 371 (c)(1),
(2), (4) Date: Nov. 15, 2005

(87) PCT Pub. No.: WO2004/101049
PCT Pub. Date: Nov. 25, 2004

(65) Prior Publication Data
US 2006/0283451 A1    Dec. 21, 2006

(30) Foreign Application Priority Data
May 15, 2003  (EP) .................................... 03425314

(51) Int. Cl.
*A61M 16/00* (2006.01)
(52) U.S. Cl. ......... 128/204.18; 128/204.26; 128/204.28; 128/205.13; 128/205.14; 128/205.17
(58) Field of Classification Search ............. 128/204.18, 128/204.26, 204.28, 204.29, 205.13, 205.14, 128/205.17, 205.24, 205.25, 205.27, 201.25, 128/201.28, 203.28, 203.29
See application file for complete search history.

(56) References Cited

U.S. PATENT DOCUMENTS

| | | | | |
|---|---|---|---|---|
| 2,300,273 A | * | 10/1942 | Connell | 128/205.17 |
| 2,376,971 A | * | 5/1945 | Kleit | 128/203.25 |
| 2,841,142 A | * | 7/1958 | Hay | 128/205.13 |
| 3,557,785 A | * | 1/1971 | McQueen | 128/205.16 |
| 5,065,756 A | | 11/1991 | Rapoport | |
| 5,148,802 A | * | 9/1992 | Sanders et al. | 128/204.18 |
| 5,301,667 A | * | 4/1994 | McGrail et al. | 128/205.14 |
| 5,613,489 A | * | 3/1997 | Miller et al. | 128/203.28 |

(Continued)

FOREIGN PATENT DOCUMENTS

WO    WO 97/10868 A    3/1997

(Continued)

*Primary Examiner* — Clinton T Ostrup
(74) *Attorney, Agent, or Firm* — Jason A. Bernstein; Barnes & Thornburg LLP

(57) ABSTRACT

An apparatus (1) for non-invasive mechanical ventilation comprises a fan (2) of Bi-level type, or BiPAP, for generating an air flow according to a succession of inspiration steps, or IPAP, and exhalation steps, or EPAP. The flow is conveyed in the aerial ducts of a patient (25) by means of a flexible tube (3) connected to a nasal mask (4). A flexible air reservoir (5) is provided pneumatically connected to the duct (3) and the nasal mask (4) in order to subtract from the inspiration flow a certain air amount before that it reaches the patient (25) at the beginning of an IPAP step. During the exhalation EPAP step, since the air flow pressure decreases automatically, there is the emptying at least partial of the flexible air reservoir (5), whereas the air exhaled by the patient exits through an opening (14) made on the nasal mask (4). This way an air exchange occurs also in the most peripheral patient's aerial ducts and the amount of gaseous exchanges is increased, reducing at the same time the duration of the treatment.

7 Claims, 2 Drawing Sheets

U.S. PATENT DOCUMENTS

| | | | | |
|---|---|---|---|---|
| 5,865,173 A * | 2/1999 | Froehlich | | 128/204.23 |
| 5,947,115 A * | 9/1999 | Lordo et al. | | 128/200.24 |
| 6,131,571 A | 10/2000 | Lampotang et al. | | |
| 6,152,129 A * | 11/2000 | Berthon-Jones | | 128/200.24 |
| 6,240,921 B1 * | 6/2001 | Brydon et al. | | 128/205.23 |
| 6,390,090 B1 * | 5/2002 | Piper | | 128/203.28 |
| 6,401,713 B1 * | 6/2002 | Hill et al. | | 128/204.21 |
| 6,739,335 B1 * | 5/2004 | Rapport et al. | | 128/204.18 |
| 6,752,150 B1 * | 6/2004 | Remmers et al. | | 128/204.18 |
| 2002/0023644 A1 * | 2/2002 | Berthon-Jones | | 128/204.22 |
| 2003/0051729 A1 * | 3/2003 | Be'eri et al. | | 128/204.18 |
| 2004/0094156 A1 * | 5/2004 | Meakin | | 128/205.13 |

FOREIGN PATENT DOCUMENTS

| | | |
|---|---|---|
| WO | WO 00/45882 A | 8/2000 |

* cited by examiner

APPARATUS FOR NON-INVASIVE MECHANICAL VENTILATION

BACKGROUND OF THE INVENTION

As known, the respiratory system, comprising lungs and thoracic cage, works as a pump that rests on a muscle called the diaphragm, which coordinates air and oxygen suction/exhalation actions. In natural ventilation a contraction of the diaphragm produces a vacuum in the lungs so that air is inspired. However, problems of respiratory insufficiency caused by thoracic cage or lungs pathologies, as well as problems of insufficient ventilation revealed by the rise of carbon dioxide in arterial blood beyond physiological values, can affect the correct operation of the respiratory system. Then, for increasing or restoring a natural ventilation in an individual in poor health, a mechanical ventilation must be applied that consists of delivering pressurized air in the aerial ducts (also known as the airways or air passages) and then in the lungs of the patient by means of a special apparatus.

A largely used technique for treatment of patients with chronic pulmonary pathologies or with acute respiratory insufficiency is Non-Invasive Mechanical Ventilation (NIMV). NIMV assures a much lighter work to respiratory muscles, improves gaseous exchanges and in most cases avoids the need of an intratracheal intubation, which is much more invasive and can cause lesions or infections of the respiratory system, as well as it can be applied only in a hospital.

An apparatus for non-invasive mechanical ventilation comprises usually a fan, which produces air at a certain pressure, and a nasal mask, which is connected to the fan by means of a flexible tube. Furthermore, pneumatic instruments are provided that control the air delivery on the basis of pressure data measured in real time, which are responsive to the respiration of the patient or are set in a predetermined pressure program.

Non-invasive ventilation with positive pressure has two particular approaches, one with fixed pressure (CPAP) and another with two levels of pressure, or bi-level (BiPAP). In particular, the BiPAP is a kind of ventilation characterized by two different levels of pressure, which exchange with each other at a predetermined interval and allow passive pulmonary ventilation responsive to changes of intrapulmonary pressure. At the same time the patient can breath spontaneously at each step of the respiratory cycle without any mechanical support. More in detail, the apparatus for ventilation delivers an inspiration positive air pressure (IPAP), by means of a fan when breathing in, and an exhalation positive air pressure (EPAP), which is also positive but less than the previous. In other words, during the mechanical ventilation, the apparatus accomplishes the respiratory work necessary to ventilate the lungs. Usually, the EPAP is only slightly more than the atmospheric pressure whereas the IPAP is much higher.

However, in the existing apparatus the air pressure supplied to the patient follows a predetermined profile depending on a program, on the kind of fan and on the kind of control chosen, and said profile hardly would fit the peculiar needs of an individual. In fact, the set limit values are IPAP and EPAP and only adjustable value is the pressure of air supplied between the two limit values, by a valve or alternatively by controlling the fan power.

Furthermore, such apparatus can assure ventilation and air exchange only to the main aerial ducts without reaching the peripheral aerial ducts, and this fact could lead to atrophy of the latter. This drawback has also the consequence of a very long time before reaching a natural respiration rate of the patient after a temporary trauma.

SUMMARY OF THE INVENTION

It is therefore a feature of the present invention to provide an apparatus for non-invasive mechanical ventilation that provides air exchange also in the most peripheral a patient's aerial ducts.

It is also a feature of the present invention to provide an apparatus for non-invasive mechanical ventilation that increases the amount of the gaseous exchanges and reduces the duration of the treatment of the fan.

These and other features are achieved by the apparatus for non-invasive mechanical ventilation, according to the present invention, comprising, in one exemplary embodiment:

a) means for generating an air flow according to a predetermined pressures cycle comprising a succession of inspiration steps, or IPAP, and exhalation steps, or EPAP, wherein each inspiration step has its apex with a maximum pressure and each exhalation step ends with a pressure of minimum; and b) means for conveying said air flow to a patient's airways; which subtracts a predetermined air amount from said flow at the beginning of said inspiration step, said means for subtracting being in pneumatic connection with said means for conveying.

In particular, the subtraction of an air amount from the inspiration flow causes a depression sufficient for creating a vortex in a patient's aerial ducts, thus allowing the air to reach the most peripheral aerial ducts.

Advantageously, said means for subtracting air comprises at least one air reservoir suitable for filling of air between the EPAP step and the following IPAP step, thus subtracting said predetermined air amount from said flow.

In particular, the reservoir can be a flexible container suitable for filling of air in the IPAP step and emptying at least in part in the EPAP step.

Alternatively, said means for subtracting can comprise a calibrated opening made in the means for conveying. In this case, the calibrated opening can be operated automatically.

In an exemplary embodiment of the invention the means for conveying comprises a duct and a nasal mask and said means for subtracting a predetermined air amount are connected to the nasal mask or to the duct by means of a junction fitting.

BRIEF DESCRIPTION OF THE DRAWINGS

Further characteristics and advantages of the present invention will be made clearer with the following description of a possible exemplary embodiment, exemplifying but not limitative, with reference to the attached drawings, wherein.

DESCRIPTION OF THE INVENTION

Figure 1:
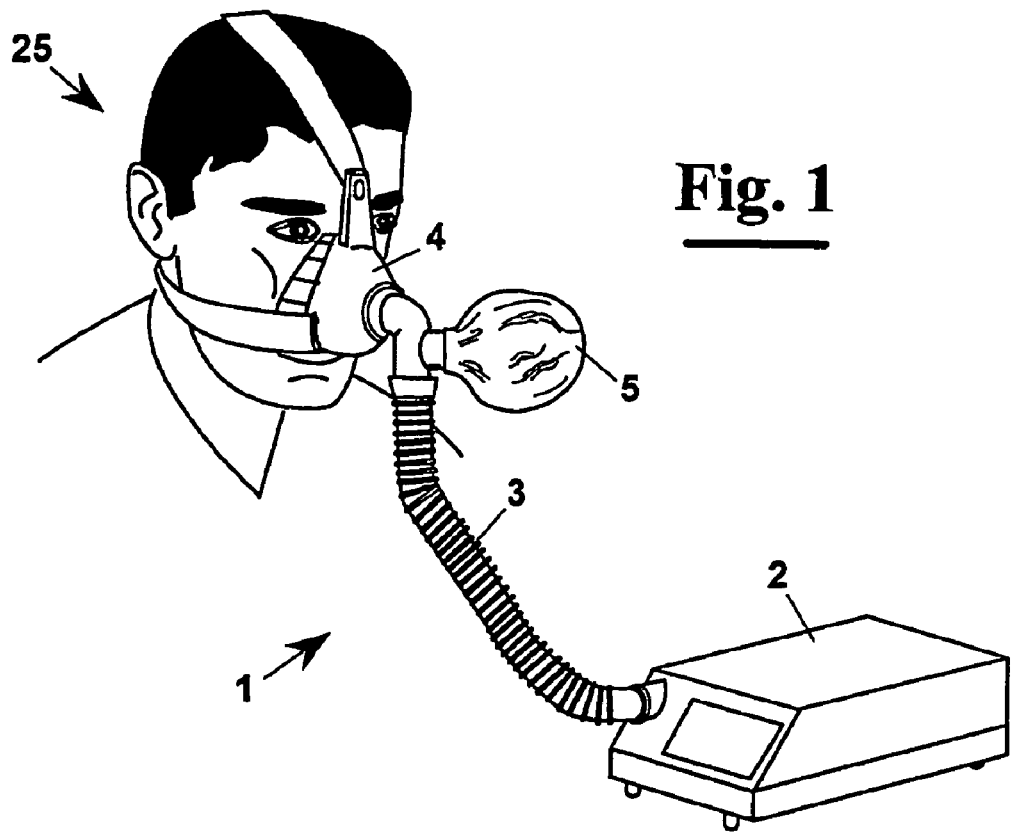
FIG. 1 shows diagrammatically a perspective view of an apparatus for non-invasive mechanical ventilation, according to one exemplary embodiment of the invention, applied to a patient.

In FIG. 1 a first exemplary embodiment is shown of a non-invasive mechanical ventilation apparatus 1, according to the present invention. It comprises a fan 2 for generating an air flow according to a predetermined pressures cycle, consisting of a succession of inspiration steps, or IPAP, and exhalation steps, or EPAP. The air flow generated by fan 2 is conveyed into the aerial ducts of a patient 25 by a flexible tube 3 connected to a nasal mask 4 worn by patient 25. The main feature of the non-invasive mechanical ventilation apparatus 1, according to the invention, is to provide a flexible air reservoir 5 arranged pneumatically connected to duct 3 and nasal mask 4, in order to subtract from the inspiration flow a certain air amount before that it reaches the aerial ducts of patient 25.

Figure 2A:
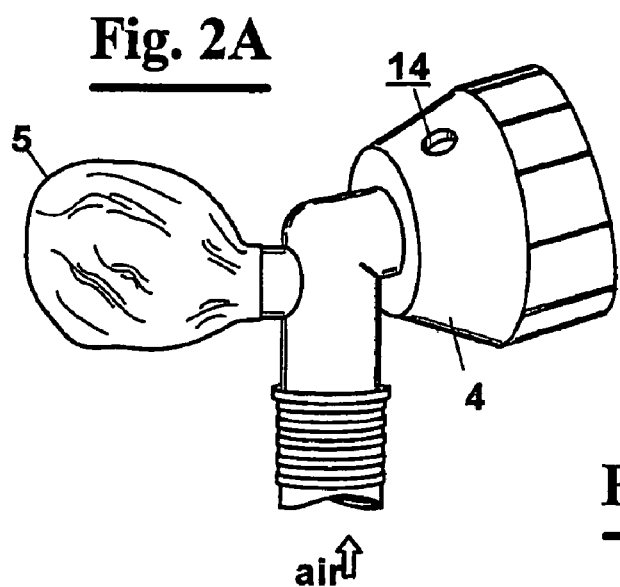
FIG. 2A shows diagrammatically a perspective view of a detail of the nasal mask of the mechanical ventilation apparatus of FIG. 1 during an IPAP step.
Figure 2B:
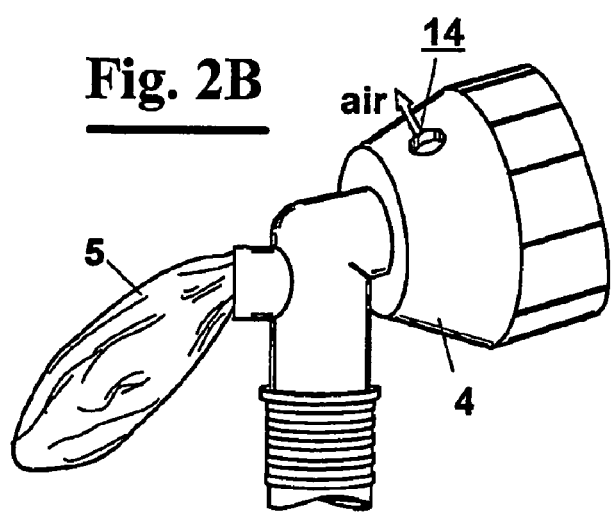
FIG. 2B shows diagrammatically a perspective view of a detail of the nasal mask of the mechanical ventilation apparatus of FIG. 1 during an EPAP step.

In particular, at the beginning of an IPAP step a certain air amount of the flow generated by fan 2 enters reservoir 5, for example a "balloon" of flexible material, preventing said air amount from reaching patient 25, who has already started the inspiration step (FIG. 2A). Then, during the exhalation step, when the air flow pressure reduces automatically owing to the low level pressure of the Bi-level fan, at least partially balloon 5 empties, while the exhaled air from the patient exits through an opening 14 made on nasal mask 4 (FIG. 2B). In fact, the higher pressure of IPAP step causes the balloon to inflate, because this pressure exceeds the own weight of the walls of the balloon. During the EPAP step, instead, the lower pressure is not sufficient to exceed the own weight of the balloon, which partially empties.

Figures 3A, 3B, 3C:
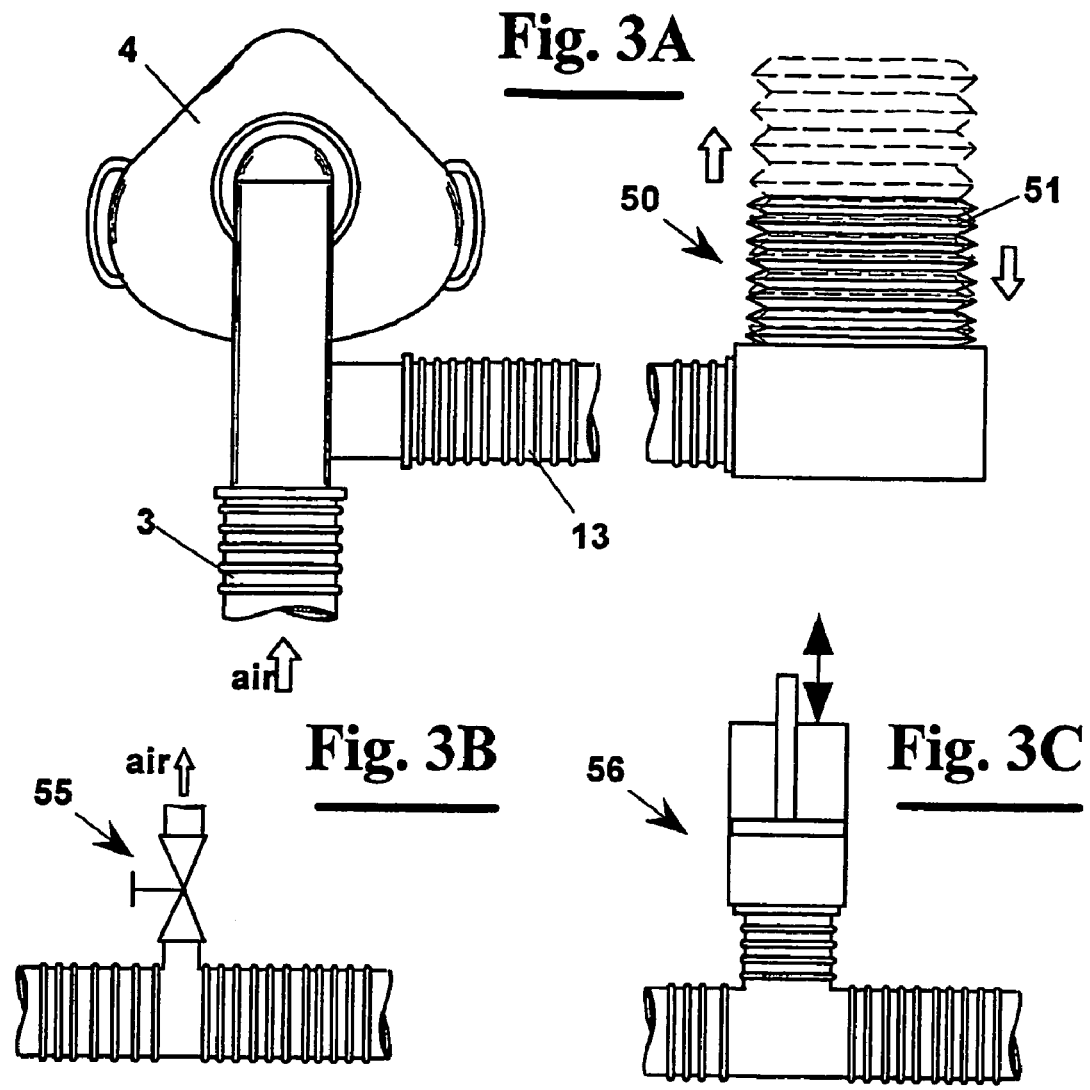
FIGS. 3A to 3C show diagrammatically three different air subtraction devices for an apparatus for non-invasive mechanical ventilation according to alternative exemplary embodiments to that shown in FIG. 1.

In FIG. 3A an air reservoir 5 is shown as an alternative exemplary embodiment to that of FIG. 1. In this case a device is used comprising an accordion-shaped reservoir 51 suitably sized in order to fill of air during the IPAP step and to empty during the EPAP step, like in the previous case. Obviously, the step of subtraction of the air can also be carried out in another desired known way. An important requirement is that the automatic operation of the BiPAP fan is not affected. For example, a calibrated valve 55 can be used delivering air in the atmosphere and whose closure/opening can be automatically operated (FIG. 3B).

In a further alternative exemplary embodiment, a pneumatic system can be provided of subtraction of air 56, where the subtracted air amount can be set in synchronism with the beginning of the IPAP step (FIG. 3C).

Figure 4:
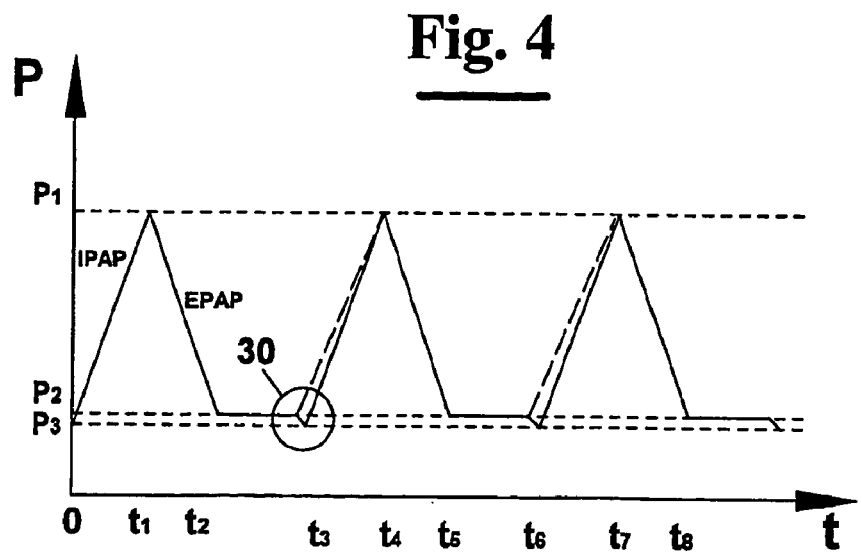
FIG. 4 shows diagrammatically the pressure trend versus time in the apparatus of FIG. 1 during a pressures cycle comprising inspiration steps, or IPAP, alternated to exhalation steps, or EPAP comparing it with the trend of the apparatus of prior art.

The above four possible exemplary embodiments have a similar result, as diagrammatically shown in FIG. 4, which illustrates the pressure trend (P) versus time (t) that is achieved during a cycle where inspiration steps, or IPAP, are alternated with exhalation steps, or EPAP. In particular, in the apparatus of prior art the final pressure $P_2$ of an IPAP step is the same as the starting pressure $P_2$ of the following EPAP step (dotted line). In contrast, the apparatus 1 according to the embodiment of the invention shown in FIG. 4 provides a light depression 30 between the final pressure $P_2$ of an IPAP step and the starting pressure $P_3$ of the following EPAP step with IPAP and EPAP exchanged between each other. The light depression caused by the difference between the pressures $P_2$ and $P_3$ is sufficient to create a vortex in the aerial ducts of patient 25 that causes the following IPAP air flow to reach the most peripheral aerial ducts. This way, a non-invasive mechanical ventilation is achieved that is more effective with respect to that obtained with the apparatus of prior art and that allows increasing gaseous exchanges as well as reducing remarkably the duration of the treatment.

Furthermore, the apparatus 1 allows achieving a further therapeutic effect on pulmonary ventilation, specifically improving ventilation in lower and more peripheral lungs sections, whereas in ventilation induced by traditional VMNI a reduction of the ventilation in medium-apex lungs sections is observed.

The foregoing description of a specific exemplary embodiment will so fully reveal the invention according to the conceptual point of view, so that others, by applying current knowledge, will be able to modify and/or adapt for various applications such an exemplary embodiment without further research and without parting from the invention, and it is therefore to be understood that such adaptations and modifications will have to be considered as equivalent to the specific exemplary embodiment. The means and the materials to realise the different functions described herein could have a different nature without, for this reason, departing from the field of the invention. It is to be understood that the phraseology or terminology employed herein is for the purpose of description and not of limitation.

The invention claimed is:

1. An apparatus for non-invasive mechanical ventilation, comprising:
   a) an air flow generator for generating an air flow deliverable to a patient's lungs and which creates a vortex in the aerial ducts of said patient's lungs, said air flow being generated according to a predetermined bi-level positive pressure cycle, said cycle comprising a succession of an Inspiration Positive Air Pressure ("IPAP") step having a pressure $P_{IPAP}$, and an Exhalation Positive Air Pressure ("EPAP") step having a pressure $P_{EPAP}$, wherein each IPAP step has its apex with a maximum pressure and each EPAP step ends with a minimum pressure, and wherein $P_{IPAP}$ is greater than $P_{EPAP}$;
   b) an air conveyance apparatus comprising a duct and a nasal mask for conveying said air flow to a patient's aerial ducts, said air conveyance apparatus when in use being arranged between said air flow generating means and said patient; and,
   c) a pneumatic air subtraction system for subtracting a predetermined air amount from said air flow, said pneumatic air subtraction system being in pneumatic connection with said air conveyance apparatus,
   wherein said pneumatic air subtraction system is adapted to subtract from said air flow a pre-determined amount of air before said determined amount of air reaches said aerial ducts for carrying out said IPAP step so as to temporarily prevent said pre-determined amount of air from reaching said aerial ducts, and
   wherein said pneumatic air subtraction system is adapted to subtract said pre-determined amount of air at the beginning of said IPAP step.

2. The apparatus according to claim 1, wherein said pneumatic air subtraction system comprises at least one air reservoir that fills with air, thus subtracting said predetermined amount of air from said air flow in synchronism with the beginning of said IPAP step.

3. The apparatus according to claim 2, wherein said air reservoir comprises a flexible container suitable for filling of air synchronized with the beginning of said IPAP step and emptying at least in part during the EPAP step.

4. The apparatus according to claim 3, wherein said flexible container comprises either a bag or a balloon.

5. The apparatus, according to claim 1, wherein said pneumatic air subtraction system comprises a calibrated hole made in said air conveyance apparatus.

6. The apparatus, according to claim 5, wherein said calibrated hole is opened and closed automatically.

7. An apparatus for non-invasive mechanical ventilation, comprising:
- a) an air flow generator for generating an air flow deliverable to a patient's lungs and which creates a vortex in the aerial ducts of said patient's lungs, said air flow being generated according to a predetermined bilevel positive pressure cycle, said cycle comprising a succession of an Inspiration Positive Air Pressure ("IPAP") step, and an Exhalation Positive Air Pressure ("EPAP") step, wherein each IPAP step has its apex with a maximum pressure and each EPAP step ends with a minimum pressure;
- b) an air conveyance apparatus comprising a duct and a nasal mask for conveying said air flow to a patient's aerial ducts, said air conveyance apparatus when in use being arranged between said air flow generating means and said patient; and,
- c) a pneumatic air subtraction system for subtracting a predetermined air amount from said air flow, said pneumatic air subtraction system
  - i. includes at least one expandable container that can be filled with or emptied of air,
  - ii. includes a hole defined in said container which can be opened or closed automatically, and
  - iii. is in pneumatic communication with said air conveyance apparatus, wherein said pneumatic air subtraction system is adapted to subtract from said air flow a pre-determined amount of air before said determined amount of air reaches said aerial ducts for carrying out said IPAP step so as to temporarily prevent said pre determined amount of air from reaching said aerial ducts, and wherein said pneumatic air subtraction system is adapted to subtract said predetermined amount of air at the beginning of said IPAP step.

* * * * *